(12) United States Patent
Zindel et al.

(10) Patent No.: US 7,291,355 B2
(45) Date of Patent: Nov. 6, 2007

(54) FERMENT ACTIVATOR BASED ON LACTIC ACID BACTERIA AND METHOD FOR PREPARING A DAIRY PRODUCT USING SAME

(75) Inventors: Laurent Zindel, Chatellerault (FR); Annie Mornet, Mondion (FR); Eloi Fontaine, Tours (FR); Denis Guillaud, Paladru (FR)

(73) Assignee: Rhodia Chimie, Aubervilliers (FR)

( * ) Notice: Subject to any disclaimer, the term of this patent is extended or adjusted under 35 U.S.C. 154(b) by 123 days.

(21) Appl. No.: 10/111,703

(22) PCT Filed: Sep. 20, 2001

(86) PCT No.: PCT/FR01/02928

§ 371 (c)(1),
(2), (4) Date: Oct. 18, 2002

(87) PCT Pub. No.: WO02/24870

PCT Pub. Date: Mar. 28, 2002

(65) Prior Publication Data

US 2003/0096037 A1    May 22, 2003

(30) Foreign Application Priority Data

Sep. 25, 2000  (FR) .................... 00 12172
Feb. 23, 2001  (FR) .................... 01 02492

(51) Int. Cl.
*A23C 9/12*    (2006.01)
(52) U.S. Cl. .................... 426/34; 426/42; 426/43; 426/61; 426/580
(58) Field of Classification Search .................... 426/34, 426/36, 40, 42, 43, 61, 580, 582, 583
See application file for complete search history.

(56) References Cited

U.S. PATENT DOCUMENTS 4,020,185 A    4/1977   Andersen et al.
4,402,986 A    9/1983   Sinkoff et al.
4,766,076 A *  8/1988   Sandine et al. .......... 435/253.6
4,806,479 A *  2/1989   Kegel et al. ................ 435/244
4,851,347 A    7/1989   Willrett et al.

FOREIGN PATENT DOCUMENTS

EP    0 575 951       12/1993
WO    WO 99/09838     3/1999

OTHER PUBLICATIONS

H.L.M. Lelieveld, "Continuous Fermentation in Yoghurt Manufacture," *Process Biochemistry*, vol. 11, No. 5, Jun. 1976, p. 39, Figure 1.
Gomes et al., "Use of small ruminants' milk supplemented with available nitrogen as growth media for *Bifidobacterium lactis* . . . ," *J. of Applied Microbiology*, vol. 85, No. 5, Nov. 1998, pp. 839-848.
Bannikova et al., "Starter for cows milk koumiss," *International Food Information Service* (*IFIS*), vol. 27 (1970), Abstract.
"Whey Powder", pp. 1-3, www.milkingredients.ca/dcp/article_e.asp?catid=145&page=210, no date.
"Dehydrated Culture Media and Reagents", Difco Manual, Tenth Edition, Difco Laboratories, Detroit Michigan (1984).

* cited by examiner

*Primary Examiner*—Leslie Wong
(74) *Attorney, Agent, or Firm*—Buchanan, Ingersoll & Rooney, PC

(57) ABSTRACT

The invention concerns a ferment activator based on lactic acid bacteria, characterised in that it comprises at least: a nitrogenous substance, a buffer system capable of maintaining the activity pH of the lactic acid bacteria with which said activator is to be associated at a value ranging between 5 and 7, and free of added sugar(s) capable of being metabolised by said lactic acid bacteria. The invention also concerns a method for preparing a dairy product characterised in that it consists in using said activator.

18 Claims, No Drawings

FERMENT ACTIVATOR BASED ON LACTIC ACID BACTERIA AND METHOD FOR PREPARING A DAIRY PRODUCT USING SAME

This application is a 371 of PCT/FR01/02928 filed Sep. 20, 2001.

The present invention relates to an activator for a ferment based on lactic acid bacteria, to the use of this activator for the preparation of milk products and to the method for preparing a milk product characterized by the use of this activator.

The fermentation of milk is generally carried out by inoculating it with a bacterial culture commonly designated by the name of starter or ferment. This ferment generally contains anaerobic or microaerophilic bacteria belonging to the group of Gram-positive bacteria which ferment sugars into their respective acids. The acid mainly produced is lactic acid from lactose.

Generally, these ferments contain mesophilic organisms having an optimum growth temperature of between 25 and 35° C. and/or said thermophilic organisms having an optimum growth temperature of between 35 and 45° C.

The organisms most widely used and which are present in ferments are those belonging to the genera *Lactococcus, Streptococcus, Lactobacillus, Leuconostoc, Pediococcus, Bifidobacterium* and *Brevilbacterium*.

The specific organisms belonging to the mesophile group comprise *Lactococcus lactis* subsp. *lactis, Lactococcus lactis* subsp. *cremoris, Lactococcus lactis* subsp. *lactis biovar. diacetylactis, Leuconostoc cremoris, Leuconostoc mesenteroides* subsp *mesenteroides, Leuconostoc mesenteroides* subsp *lactis*, this list not being exhaustive.

These thermophilic type bacterial species are, inter alia, *Streptococcus thermophilus, Lactobacillus casei, Lactobacillus paracasei, Lactobacillus helveticus, Lactobacillus delbrueckii* subsp. *Bulgaricus, Lactobacillus bulgaricus* and *Lactobacillus acidophilus*.

These ferments are used in a concentrated form or in a dry form, that is to say in the form of a powder, for example a freeze-dried or spray-dried powder, in a liquid form, or in a frozen state.

These types of formulation have the double advantage of preserving the viability of the cultures over a long period and of being most particularly appropriate for direct inoculation, according to which the ferment is directly introduced into the manufacturing milk. Advantageously, no preliminary culturing is found to be necessary before use unlike the so-called semidirect inoculation.

Although the present invention can also be effectively applied to semidirect inoculation, it is found to be most particularly advantageous for the so-called direct inoculation for the following reason: when the bacteria are introduced during a direct inoculation, that is to say in the form of a dry, liquid or frozen concentrate, they are not immediately effective and they require a restoration of activity. The restoration of activity of this type of ferment requires a lapse of time for adaptation corresponding, on the one hand, to the revival of the bacterium packaged in its natural form and, on the other hand, to the restoration of its metabolic activity. More precisely, this adaptation time successively comprises a first phase for rehydration and a second so-called "latent" phase corresponding more particularly to the "reawakening" of the metabolic activity of the bacteria. It is during this second phase that cellular repair, adaptation of the enzymatic system to its biological environment and initiation of cell division occur. Whereas the rehydration phase is practically immediate, the latent phase may extend up to 3 hours, and is of course damaging for the industrialist in terms of profitability.

The direct inoculation technique offers decisive advantages: immediate availability of the ferments with a reduced hindrance, possibility of preparing complex mixtures of different species or strains in defined and constant proportions, increased regularity of performance compared with traditional ferments prepared at the sites of use, production carried out in specialist units where each stage of the method is optimized and controlled, the quality of the ferments vigorously defined.

The objective of the present invention is precisely to provide a means for significantly reducing this latent period.

Unexpectedly, the inventors have demonstrated that the bringing into contact of a ferment based on lactic acid bacteria and preferably so-called direct contact, with an activator in accordance with the invention, prior to its introduction into the milk medium to be treated, made it possible to significantly reduce said latent period.

The first subject of the present invention is therefore an activator for a ferment based on lactic acid bacteria.

Its second subject is the use of this activator to activate, in liquid medium, a ferment based on lactic acid bacteria.

Another aspect of the present invention relates to a ferment based on lactic acid bacteria thus activated.

Finally, the fourth subject of the present invention is a method for preparing a milk product, characterized by the use of this activator or of an activated ferment according to the invention.

More precisely, the present invention relates to an activator for a ferment based on lactic acid bacteria, characterized in that it comprises at least:
  a nitrogenous substance,
  a buffer system capable of maintaining the pH for activity of the lactic acid bacteria with which said activator has to be combined at a value between 5 and 7,
  and which is free of added sugar(s) which can be metabolized by said lactic acid bacteria.

The claimed activator is particularly advantageous in terms of stability and/or of gain in productivity, of a ferment for direct inoculation in liquid form.

Accordingly, because of the absence, from the activator, of metabolizable sugar(s), no substantial production of lactic acid which would be damaging to the stability of the lactic acid bacteria is initiated during the bringing of this activator into contact with the ferment to be activated. Greater stability over time of the activated ferment follows.

Consequently, the joint use of the activator with a ferment based on lactic acid bacteria advantageously makes it possible to preserve and standardize the metabolic activity of the activated bacteria over a prolonged period of time compared with that observed with an identical ferment in a nonactivated form.

Furthermore, quite advantageously, the use of the activator with a ferment makes it possible to delay cell multiplication or quite simply to limit cell multiplication, while allowing the ferments to resume their metabolic activity and while maintaining the activated ferment according to the invention effective. This is illustrated by example 3.

An activated ferment according to the invention is advantageously effective over a period extending up to 72 hours, more particularly over a period extending up to 48 hours, preferably over a period extending up to 24 hours.

Accordingly, a ferment based on an activated *Lactococcus lactis* according to the invention is effective over a period extending up to 72 hours whereas an identical, but nonactivated, ferment manifests a significant loss of activity above 3 hours.

Moreover, the inventors have observed that the presence of the activator was advantageous in terms of equilibrium of microbial populations in the activated system. This is in particular illustrated in example 3 presented below.

As regards gain in productivity, it is mainly linked to the reduction of the so-called "latent" period.

More precisely, for the purposes of the present invention, the expression "latent period" designates the period elapsing between the moment of introducing the activated or nonactivated ferment into a milk product and the moment where the metabolic activity of the lactic acid bacteria present in this ferment is verified by a significant reduction of the pH of the milk medium due to the formation of lactic acid. This so-called significant reduction in the pH is in fact an arbitrary value which depends on the measuring apparatus selected. However, as a guide and in the case of the apparatus used in the examples illustrating the invention, this reduction in the pH is evaluated at about 0.08. More generally, it can be estimated that this significant reduction is reached when the pH of the milk medium treated has decreased by about 5% of its initial value.

This gain in productivity is particularly significant for ferments based on lactic acid bacteria comprising totally or at the very least predominantly mesophilic-type bacteria. Advantageously, the combination of an activator with a ferment based on mesophilic-type lactic acid bacteria reduces the latent period by about 10 to 25% of its standard value.

Consequently, and as is evident from the examples presented below, a ferment based on lactic acid bacteria in a freeze-dried form, mixed prior to its introduction into the milk with an activator according to the invention, restores an acidifying power in the milk much more rapidly compared with the standard ferment, that is to say in a nonactivated form.

The nitrogenous substances present in the claimed activator are or result preferably from nitrogenous substances of the peptide and amino acid type and/or from one or more dairy or nondairy proteins.

By way of representatives of the proteins suitable for the invention, there may be mentioned in particular β-lactoglobulin, albumin and alpha-lactalbumin, caseins and derivatives such as lactic casein, rennet casein and caseinates, kappa-casein and beta-casein.

As other examples of nitrogenous substances, there may be mentioned in particular yeast extracts and more preferably an extract of the yeast *Saccharomyces cerevisiae*, which may be combined with the proteins cited above.

This fraction with nitrogenous substances constitutes about 50 to 90%, and preferably 60 to 80% by weight of the activator.

The activator according to the invention does not contain added sugar(s), which means that there cannot be other sources of added sugar(s) in this activator other than the nitrogenous substances.

It is indeed not excluded that these nitrogenous substances may contain a certain quantity of metabolizable sugar(s), according to the source of nitrogenous substances used.

As regards the buffer medium, its main role is to stabilize the pH of the activated ferment at a value close to between 5 and 7 during the period for its reactivation. Its presence proves particularly advantageous when it is intended to be combined with a ferment mainly comprising mesophilic and thermophilic type lactic acid bacteria.

By way of illustration of the buffer mixtures which may be suitable for the invention, there may be mentioned in particular those comprising salts such as magnesium and calcium salts as well as carbonate, phosphate and citrate salts.

They are preferably a mixture of carbonates and more preferably a mixture of calcium carbonate and magnesium carbonate.

According to a variant of the invention, nutritive elements which are useful for maintaining the metabolic activity of the lactic acid bacteria are also combined with the nitrogenous substances and the buffer mixture.

These nutritive elements generally include vitamins.

Likewise, cofactors useful for activating glycolysis may be present in the claimed activator. As representative of these cofactors, there may be mentioned in particular the inorganic salts $Ca^{2+}$, $Mg^{2+}$, $Mn^{2+}$, $Cu^{2+}$ and $Zn^{2+}$. They are generally used in an amount of 0.1 to 2%.

It is also possible to envisage incorporating into the activator texturing agents of the hydrocolloid type, such as xanthan gum, guar gum, and the like.

More precisely, the activator according to the invention is free of added sugar(s) which can be metabolized by said lactic acid bacteria.

Still more precisely, the activator according to the invention comprises at most 15% by weight of sugars which can be metabolized by said lactic acid bacteria, preferably at most 10% of said sugars, and more particularly at most 5% of said sugars. It is understood that they include sugar(s) not added in the sense defined above.

By way of illustration of the claimed activators, there may be mentioned more particularly those comprising at least calcium caseinate, in an amount of 20 to 40% by weight, and as buffer mixture, a mixture of calcium carbonates and of magnesium carbonates. Yeast extracts and manganese sulfate are also preferably present in this activator.

The claimed activator may be obtained by simply mixing its components and is generally present in a dry, generally pulverulent, form. However, it is also possible to envisage formulating it in a freeze-dried or frozen form.

The claimed activator may also be provided in liquid form.

According to a preferred variant of the invention, the claimed activator is provided in a sterilized form and is used while preserving this sterile aspect.

The second subject of the present invention is the use of an activator in accordance with the present invention for activating a ferment based on lactic acid bacteria prior to or during the inoculation of a milk medium.

The ferment to activator ratio is between 10% and 70% by dry weight, preferably 20% to 60% by dry weight.

The use of this activator to activate, in liquid medium, a ferment based on lactic acid bacteria has the advantage of an on-line, automatable, continuous or batch and aseptic inoculation.

The subject of the invention is also an activated ferment based on lactic acid bacteria, characterized in that it combines an activator in accordance with the invention with at least lactic acid bacteria.

In this instance, the claimed activator is used in a quantity such that these components, namely the nitrogenous substances and buffer mixture, are present in sufficient quantities for a significant activation of the ferment based on lactic acid bacteria to be observed.

As a guide, it is used in a quantity such that its content of nitrogenous substances is adjusted in an amount of about 160 to 300% by weight relative to the weight of lactic acid bacteria present in the ferment to be activated, preferably about 160% to 250%.

The activator may be mixed with the ferment either beforehand or at the time of its use. However, according to a preferred embodiment, prior to its use, it is rehydrated in the presence of an activator in accordance with the present invention. Generally, this combination is carried out in a liquid medium, preferably water.

The activator is rehydrated such that the quantity of activator is between 5% and 20% by weight of aqueous suspension, preferably between 7% and 15%.

The rehydration and consecutive activation may be carried out at a temperature between 10° C. and 20° C. and preferably with stirring, so as to optimize activation and homogenization over time. The activated ferment is then used as it is for the inoculation, preferably direct inoculation, of a milk medium.

The lactic acid bacteria capable of being combined with an activator in accordance with the invention include all the bacteria customarily used for the production of milk products.

As a guide for lactic acid bacteria, there may be mentioned the bacteria belonging to the genera *Lactococcus, Streptococcus, Lactobacillus, Leuconostoc* and *Pediococcus*.

The bacteria used in the dairy sector which belong to the genera *Bifidobacterium, Propionibacterium* and *Brevibacterium* are also considered as lactic acid bacteria.

They may also be microorganisms more particularly used for ripening and in particular used in the cheese industry. By way of representatives of this second type of microorganisms, there may be mentioned in particular *Penicillium roqueforti, Penicillium candidum, Geotrichum candidum, Tourla kefir* and *Saccharomyces kefir* and *Kluyveryomyces lactis*.

The fourth subject of the present invention is a method for preparing a milk product comprising:
(i) bringing a ferment based on lactic acid bacteria into contact with an activator in accordance with the present invention, so as to obtain a so-called activated ferment,
(ii) inoculating the milk medium to be treated, preferably milk, with said ferment in an activated form, and
(iii) incubating said milk medium under conditions favorable to the metabolic activity of the lactic acid bacteria, so as to obtain the expected milk product.

For the purposes of the present invention, the ferment obtained after the first stage (i) is so-called activated since compared with its standard form, that is to say not combined with an activator according to the invention, it manifests an improved bacterial activity. This improvement manifests itself in terms of stability and gain in productivity as discussed above.

As regards the preliminary stage (i), namely the bringing of the ferment into contact with the claimed activator, it is generally carried out within a period sufficient for the production of the activated form and in a liquid medium. The corresponding suspension may be obtained by adding a liquid, preferably an aqueous medium, to the mixture of the two components or by consecutive dispersion of the two components in said liquid.

As specified above, the activator is used in a quantity such that its content of nitrogenous substances is adjusted to an amount of about 160 to 300% by weight relative to the weight of lactic acid bacteria, preferably about 160% to 250%.

The use of the method according to the invention may be carried out by means of an inoculation device.

The preferred inoculation device, for carrying out the method according to the invention, is provided in the form of a sealed reservoir.

The sealed reservoir may be provided in the form of a closed pouch provided with an internal stirring system and inlet and outlet means.

One of the inlet means allows the arrival of the aqueous medium in the sealed reservoir in order to carry out step (i). The aqueous medium is sterilized beforehand, preferably it is filtered on a membrane of at most 0.45 µm, more particularly at most 0.22 µm. It should be noted that tap water can be used.

The temperature of the aqueous medium on its arrival in the sealed reservoir is between 5° C. and 15° C., preferably between 8° C. and 12° C.

One of the other inlet means allows the arrival of gas into the sealed reservoir. The arrival of gas will allow the use of the internal stirring system of the receptacle.

The internal stirring system consists of a permeable internal pouch. In this case, the sealed reservoir comprises a permeable internal pouch and a closed external pouch. The stirring is carried out by successive injection of gas into the permeable internal pouch, which allows the transfer of the suspension from the permeable internal pouch to the closed external pouch.

A gas is advantageously used which is not involved in respiration and/or oxidation in the microorganisms, the ferments and the bacteria.

The injected gas is a chemically and biologically inert gas, preferably argon, more particularly nitrogen or carbon dioxide, is injected.

The expression biologically inert gas is understood to mean a gas which is not involved in the multiplication and degradation of the microorganisms.

The gas pressure in the sealed reservoir, during the stirring, is less than 5 bar, preferably less than 1 bar.

The injection of gas can also be carried out over a regular time interval. Preferably, the gas is injected under pressure over a time interval of between 0.5 minute and 60 minutes.

The stirring allows the suspension of the ferments and of the activator in the aqueous medium.

After stirring, the suspension of ferments and of the activator is maintained in suspension by injection of gas according to the same principle of successive injection of gas into the internal pouch.

The emptying of the sealed reservoir is carried out aseptically by the outlet means, which makes it possible to carry out step (ii) of the method.

This emptying is carried out by injecting gas inside the sealed reservoir, or by transferring the aqueous suspension of ferments and of activator using a pump or by gravity.

The inoculation of the milk medium to be treated with said ferment in an activated form (step (ii)) is carried out at a flow rate of between 10 ml/min and 1000 ml/min, preferably of between 100 ml/min and 500 ml/min.

Step (ii) according to the invention is carried out at a temperature of between 5° C. and 40° C., preferably of between 10° C. and 15° C.

Step (ii) according to the invention is carried out over a period extending up to 72 hours, more particularly over a period extending up to 48 hours, preferably over a period extending up to 24 hours.

Step (ii) may be carried out according to several variants.

A first variant of the method at the level of step (ii) consists in inoculating the milk medium to be treated once with said ferment in an activated form. This is carried out by emptying the reservoir(s) in a single operation. This involves a batch inoculation (a single reservoir) or a multi-batch inoculation (several reservoirs).

A second variant of the method at the level of step (ii) consists in inoculating the milk medium to be treated continuously with said ferment in an activated form.

A third variant of the method at the level of step (ii) consists in inoculating the milk medium to be treated batchwise with said ferment in an activated form.

The expression batchwise is understood to mean an inoculation cycle performed in the following manner: the milk medium to be treated is inoculated over a lapse of time, then the inoculation is stopped, and then the inoculation is resumed, this being for several cycles.

In the context of this third variant, the inoculation of the milk medium to be treated with said ferment in an activated form (step (ii)) is carried out at a flow rate of between 10 ml/min and 1000 ml/min, preferably between 100 ml/min and 500 ml/min, carried out for a regular or irregular time interval of between 1 minute and 600 minutes.

It should be noted that the sealed reservoir is advantageously attached to a mobile station which can be moved over all the parts of the industrial chain, before or after step (i) of the method according to the invention.

The type of reservoir preferred for carrying out the method according to the invention is of the disposable and/or sterile type.

This reservoir preferably consists of a flexible material such as, for example, polypropylene, polyester, polyamide, cellulose or any other flexible material compatible with food products, preferably it is made of polyethylene.

The advantage of using the method according to the invention by means of the inoculation device as described above is to carry out a direct inoculation, at room temperature, which is sterile, standardized and adaptable to each type of production and which ensures the bacteriological quality.

Another advantage of using the method according to the invention by means of the inoculation device as described above is to make the inoculation step of the lactic ferment simple and reliable.

The present invention also extends to the various forms for packaging the claimed activator.

It is indeed possible to formulate the claimed activator in a packaging distinct from that of the ferment based on lactic acid bacteria with which it is intended to be combined or, by contrast, to envisage a common packaging in which the claimed activator and the ferment based on lactic acid bacteria are present, separately or otherwise.

This second packaging variant may in fact be designed so that it is suitable for mixing the ferment and the activator beforehand and therefore for the preparation of the so-called activated ferment prior to the inoculation of a milk medium.

The examples given below are presented by way of illustration and without limiting the present invention.

Method

The lactic acid bacteria, alone or as a mixture, exhibit a great diversity of behavior. In the case of the present invention, the acidifying activity was selected as criterion for characterization.

The acidification of a milk medium occurs according to the following chronological order:
inoculation of a milk (pH close to 6.6),
increase in the population of lactic acid bacteria by virtue of the hydrolysis of the milk lactose,
production of lactic acid by the bacteria which results in a decrease in the pH of the milk medium,
interruption of the growth of the bacteria which are gradually inhibited by the lactic acid formed,
continuation of the production of acid up to a pH of 4.5.

The acidifying activity was assessed in the examples below using an automated system for the monitoring and characterization of lactic ferments by acquisition of measurement of pH in real time, also designated below by the name CINAC.

CINAC is composed:
of Ingold type combination glass electrodes (24 channels for measurements of pH placed in Erlenmeyer flasks containing the inoculated medium and 8 channels for measurements of temperature)
of a water bath regulated by a thermostat and in which the Erlenmeyer flasks are placed
of an electronic card providing an analog signal and an electronic interface converting the latter to a digital signal
of a PC microcomputer equipped with CINAC software offering the following functions:
configuration of the system
data acquisition, treatment and storage
calibration of the probes at pH 7 and pH 4
calculation of the kinetic descriptors
graphical representations of the processed data
conversions of the data for the use of these data on other software packages
programming of heat cycles in order to regulate the temperature of the water bath
adjustment of the temperatures in order to correct variations in the latter relative to the pH (this correction is made by means of a PID regulator: proportional-integral-derivative)
execution of procedures for testing calibration data in order to detect the dysfunctions linked to the probes.

CINAC processes the data by providing kinetics of acidification curves and the descriptors of the latter.

The curves describing the kinetics represent variations in the pH and in the rate of acidification (dpH/dt), as a function of time. They reflect various stages of growth: readaptation phase, acceleration, exponential phase, slowing down, stationary phase.

The descriptors selected in examples for characterizing the kinetics of acidification are:

Ta=latent period in min (time after which the pH varied 0.08 upH below its initial value)

Vm=maximum rate of acidification in upH/min (rate taken at the maximum of the absolute value of the derivative dpH/dt=f(t))

time 5.20=time to obtain a pH of 5.20 in minutes.

From all these parameters, it is possible to assess a gain or a loss in productivity.

EXAMPLE 1

Preparation of a Rehydrated Concentrated Ferment According to the Invention

Firstly, the activator according to the invention is prepared in a sterile 1 l bottle containing a 45 mm double ring magnetic bar. The various components of this mixture are presented in table I below:

TABLE I

| Products | Quantity (g) |
| --- | --- |
| Dairy proteins | 30 |
| Extract of *S. cerivisiae* | 35 |
| Calcium carbonate | 10 |
| Magnesium carbonate | 10 |
| Manganese sulfate | 5 |

The protein and mineral fractions constituting this mixture are pasteurized at 85° C. for 30 minutes and then they are mixed and the whole is freeze-dried.

In the examples below, the activator thus obtained is then mixed with 50 g of freeze-dried ferment and 870 g of sterile water. The dry mixture is poured into water, with magnetic stirring, and the dissolution occurs within a few minutes. 1 liter of a solution which contains 50 g of freeze-dried product is thus obtained.

The temperature for rehydration of the resulting mixture, namely freeze-dried product and claimed activator, is conducted according to a so-called "winter" heat cycle. This cycle restores the rise in temperature of a combination of 25 l which starts at 15° C. and ends at a temperature of 20° C. which is reached in about 20 h.

EXAMPLE 2

Measurement of the Acidifying Activity of the Liquid Concentrate Obtained According to Example 1

The activity of the bacterial concentrate is assessed as a function of the storage time. It is measured after 20 minutes (considered as time T0), 3 hours, 6 hours, 16 hours and 24 hours of storage.

The strains tested are predominantly mesophilic strains. They are more precisely the strains RA 024, RM 034 and MA 014 which are lactic ferments marketed by RHODIA FOOD S.A.S.

The strain RA 024 is a mixture of *Lactococcus lactis* subsp. *lactis*, *Lactococcus lactis* subsp. *cremoris* and *Streptococcus salivarius* subsp. *thermophilus*.

The strain MA 014 is a mixture of *Lactococcus lactis* subsp. *lactis* and *Lactococcus lactis* subsp. *cremoris*.

The strain RM 034 is a mixture of *Lactococcus lactis* subsp. *lactis*, *Lactococcus lactis* subsp. *cremoris*, *Lactococcus lactis* subsp. *lactis biovar diacetylactis* and *Streptococcus thermophilus*.

The inoculation carrier used is semiskimmed milk at 30° C.

Because of the concentration, a dilution is made in order to be able to inoculate the acidification tests.

A control activity is started for each test carried out which uses 1 g of freeze-dried product in 200 ml of milk.

The controls are direct inoculations with nonactivated ferment in manufacturing milk.

Because of the concentration of ferments used, a dilution of the product is carried out. Thus 1 g of ferment is dissolved in 200 ml of milk which is used for the measurement of activity.

In the case of the rehydrated tests, a dilution is also carried out.

The inoculation should be carried out immediately so as not to penalize the activity of the bacterial concentrate.

Measurement of the Acidifying Activity Over Time

The results obtained with each of the strains are presented in tables II, III and IV below.

The data presented in these tables show the gains obtained in terms of stability and productivity with the activated ferments according to the invention compared with their respective nonactivated form.

TABLE II

| A 014 activated | Test activated then stored | | | | | |
|---|---|---|---|---|---|---|
| Storage time | 1 H | 2 H | 4 H | 6 H | 8 H | 24 h |
| Time in min to have a pH of 5.20 MA 014 nonactivated control | 380 | 370 | 385 | 385 | 380 | 380 |
| Time in min to have a pH of 5.20 | 400 | 400 | 400 | 400 | 400 | 400 |

TABLE II-continued

| A 014 activated | Test activated then stored | | | | | |
|---|---|---|---|---|---|---|
| Storage time | 1 H | 2 H | 4 H | 6 H | 8 H | 24 h |
| Technological gain in time in minutes obtained with the activated form | 20 | 30 | 15 | 15 | 20 | 20 |

TABLE III

| RA 024 activated | Test activated then stored | | | | | | |
|---|---|---|---|---|---|---|---|
| Storage time | 1 H | 2 H | 4 H | 6 H | 8 H | 12 H | 24 h |
| Time in min to have a pH of 5.20 RA 024 nonactivated control | 395 | 395 | 390 | 390 | 390 | 390 | 395 |
| Time in min to have a pH of 5.20 | 410 | 410 | 410 | 410 | 410 | 410 | 410 |
| Technological gain in time in minutes obtained with the activated form | 15 | 15 | 20 | 20 | 20 | 20 | 15 |

TABLE IV

| RM 034 activated | Test activated then stored | | | | | | |
|---|---|---|---|---|---|---|---|
| Storage time | 1 H | 2 H | 4 H | 6 H | 8 H | 12 H | 24 h |
| Time in min to have a pH of 5.20 RM 034 nonactivated control | 425 | 425 | 425 | 420 | 415 | 415 | 415 |
| Time in min to have a pH of 5.20 | 445 | 445 | 445 | 445 | 445 | 445 | 445 |
| Technological gain in time in minutes obtained with the activated form | 20 | 20 | 20 | 25 | 30 | 30 | 30 |

EXAMPLE 3

Stability of the Microbial Populations in the Presence of an Activator in Accordance with the Invention In this test, the stabilization of the populations is evaluated over a period of 24 hours in the rehydrated ferments RA 021, RA 022, RA 024 and RA 026 in the presence of the activator prepared according to example 1.

RA 021, RA 022 and RA 026 are strains comprising a mixture of mesophilic and thermophilic bacteria similar to that identified for the strain RA 024 and are marketed by RHODIA FOOD S.A.S.

The conditions for mixing the ferment based on lactic acid bacteria considered and the activator are identical to those presented in example 2.

The results are presented in table V below.

TABLE V

| Commercial mixtures | Group of strains | Storage time | | | |
|---|---|---|---|---|---|
| | | T 0 | 4 h 00 | 8 h 00 | 24 h 00 |
| RA021 | mesophile | 3.10E + 10 | 3.30E + 10 | 3.50E + 10 | 3.20E + 10 |
| | thermophile | 5.10E + 09 | 5.00E + 09 | 5.40E + 09 | 6.50E + 09 |
| RA022 | mesophile | 3.10E + 10 | 3.00E + 10 | 3.00E + 10 | 3.00E + 10 |
| | thermophile | 3.20E + 09 | 4.00E + 09 | 4.40E + 09 | 5.90E + 09 |
| RA024 | mesophile | 3.20E + 10 | 3.50E + 10 | 3.00E + 10 | 3.40E + 10 |
| | thermophile | 4.90E + 09 | 5.30E + 09 | 5.80E + 09 | 6.70E + 09 |
| RA026 | mesophile | 2.40E + 10 | 2.60E + 10 | 2.50E + 10 | 2.20E + 10 |
| | thermophile | 3.70E + 09 | 4.20E + 09 | 4.00E + 09 | 4.00E + 09 |

The advantageous behavior of the activator toward the bacterial population present in the ferment, and in particular the low cell multiplication are evident from these results.

The invention claimed is:

1. A method for the activation of a ferment based on lactic acid bacteria, prior to or during direct inoculation into a milk medium, comprising bringing said ferment into contact with an activator for said ferment which comprises at least:
a nitrogenous substance,
a buffer system capable of maintaining the pH for activity of the lactic acid bacteria with which said activator has to be combined at a value between 5 and 7,
and which comprises at the most 15% by weight of sugars which can be metabolized by said lactic acid bacteria, the activator thus delaying or limiting cell multiplication, while allowing the ferment to resume its metabolic activity.

2. The method according to claim 1, wherein said activator is brought into contact with the ferment based on lactic acid bacteria in a liquid medium.

3. A method for preparing a milk product comprising:
(i) bringing a ferment comprising at least lactic acid bacteria into contact witch an activator for said ferment which comprises at least:
a nitrogenous substance,
a buffer system capable of maintaining the pH for activity of the lactic acid bacteria with which said activator has to be combined at a value between 5 and 7,
and which comprises at the most 15% by weight of sugars which can be metabolized by said lactic acid bacteria, the activator thus delaying or limiting cell multiplication, while allowing the ferment to resume its metabolic activity, so as to obtain the ferment in an activated form,
(ii) inoculating the milk medium to be treated with said ferment in an activated form, and
(iii) incubating said milk medium under conditions favorable to the metabolic activity of said lactic acid bacteria so as to obtain the expected milk product.

4. The method as claimed in claim 3, wherein the method may be carried out by means of an inoculation device.

5. The method as claimed in claim 4, wherein the inoculation device is provided in the form of a sealed reservoir.

6. The method as claimed in claim 5, wherein the sealed reservoir may be provided in the form of a disposable reservoir and/or attached to a mobile station.

7. The method as claimed in claim 5, wherein the sealed reservoir may be provided in the form of a pouch provided with an internal stirring system and inlet and outlet means.

8. The method as claimed in claim 5, wherein one of the inlet means alilows the arrival of the aqueous medium in the sealed reservoir in order to carry out step (i).

9. The method as claimed in claim 5, wherein the temperature of the aqueous medium on its arrival in the sealed reservoir is between 50° C. and 150° C.

10. The method as claimed in claim 5, wherein one of the other inlet means allows the arrival of gas into the sealed reservoir.

11. The method according to claim 5, wherein the injected gas is a chemically and biologically inert gas.

12. The method as claimed in claim 5, wherein the gas pressure in the sealed reservoir is less than 5 bar.

13. The method as claimed in claim 5, wherein the injection of gas is carried out between 0.5 minute and 60 minutes.

14. The method as claimed in claim 3, wherein step (ii) may be carried out according to several variants, either in batches, or in multi-batches, or continuously or batchwise.

15. The method as claimed in claim 3, wherein step (ii) is carried out at a flow rate of between 10 ml/mm and 1,000 ml/mm.

16. The method as claimed in claim 3, wherein step (ii) is carried out at a temperature of between 50° C. and 40° C.

17. The method as claimed in claim 3, wherein step (ii) is carried out over a period extending up to 72 hours.

18. The method as claimed in claim 3, wherein the ferment based on lactic acid bacteria is brought into contact with said activator in a liquid medium.

* * * * *